United States Patent
Won et al.

(10) Patent No.: US 12,030,967 B2
(45) Date of Patent: Jul. 9, 2024

(54) PREPARATION METHOD OF SUPER ABSORBENT POLYMER

(71) Applicant: LG Chem, Ltd., Seoul (KR)

(72) Inventors: Tae Young Won, Daejeon (KR); Jungmin Sohn, Daejeon (KR); Hyemin Lee, Daejeon (KR); Junwye Lee, Daejeon (KR); Seongbeom Heo, Daejeon (KR); Kwangin Shin, Daejeon (KR); Chang Hun Han, Daejeon (KR)

(73) Assignee: LG Chem, Ltd., Seoul (KR)

( * ) Notice: Subject to any disclaimer, the term of this patent is extended or adjusted under 35 U.S.C. 154(b) by 828 days.

(21) Appl. No.: 17/057,790

(22) PCT Filed: Oct. 1, 2019

(86) PCT No.: PCT/KR2019/012832
§ 371 (c)(1),
(2) Date: Nov. 23, 2020

(87) PCT Pub. No.: WO2020/116760
PCT Pub. Date: Jun. 11, 2020

(65) Prior Publication Data
US 2021/0230316 A1    Jul. 29, 2021

(30) Foreign Application Priority Data
Dec. 7, 2018    (KR) .......................... 10-2018-0157082

(51) Int. Cl.
*C08F 2/44* (2006.01)
*B01J 20/26* (2006.01)
*B01J 20/30* (2006.01)
*C08F 2/01* (2006.01)
*C08F 220/06* (2006.01)
*C08J 3/24* (2006.01)
*C08J 9/08* (2006.01)
*C08J 9/36* (2006.01)

(52) U.S. Cl.
CPC .............. *C08F 2/44* (2013.01); *B01J 20/267* (2013.01); *B01J 20/3064* (2013.01); *C08F 2/01* (2013.01); *C08F 220/06* (2013.01); *C08J 3/245* (2013.01); *C08J 9/08* (2013.01); *C08J 9/36* (2013.01); *B01J 2220/68* (2013.01); *C08J 2201/026* (2013.01); *C08J 2333/08* (2013.01)

(58) Field of Classification Search
CPC .... B01J 20/261; B01J 20/267; B01J 2220/68; C08F 2/48; C08F 120/06; C08F 222/102; C08J 3/075; C08J 3/12; C08J 3/24; C08J 3/245; C08J 9/14; C08J 9/16; C08J 9/32; C08J 220/02; C08J 2201/026; C08J 2203/14; C08J 2203/22; C08J 2205/022; C08J 2207/12; C08J 2333/02; C08K 9/10; C08K 2201/003
See application file for complete search history.

(56) References Cited

U.S. PATENT DOCUMENTS

| | | |
|---|---|---|
| 4,883,478 A | 11/1989 | Lerailler et al. |
| 5,562,646 A | 10/1996 | Goldman et al. |
| 6,187,828 B1 | 2/2001 | Woodrum et al. |
| 2004/0092688 A1 | 5/2004 | Dairoku et al. |
| 2008/0194863 A1 | 8/2008 | Weismantel et al. |
| 2008/0200623 A1 | 8/2008 | Weismantel et al. |
| 2008/0221282 A1 | 9/2008 | Weismantel et al. |
| 2008/0275195 A1 | 11/2008 | Weismantel et al. |
| 2011/0088806 A1 | 4/2011 | Nogi et al. |
| 2011/0111231 A1 | 5/2011 | Kruger et al. |
| 2011/0313113 A1 | 12/2011 | Sakamoto et al. |
| 2012/0258851 A1 | 10/2012 | Nakatsuru et al. |
| 2013/0005926 A1 | 1/2013 | Kanzaki et al. |
| 2013/0007940 A1 | 1/2013 | Ryerson |
| 2013/0026412 A1 | 1/2013 | Machida et al. |
| 2013/0101851 A1 | 4/2013 | Takaai et al. |

(Continued)

FOREIGN PATENT DOCUMENTS

| | | |
|---|---|---|
| EP | 1418000 A2 | 5/2004 |
| EP | 2399944 A1 | 12/2011 |

(Continued)

OTHER PUBLICATIONS

International Search Report for Application No. PCT/KR2019/012832 dated Jan. 17, 2020, 5 pages.
Odian, Principles of Polymerization, Second Edition, Copyright 1981 by John Wiley & Sons, Inc, p. 203.
Schwalm, UV Coatings; Basics, Recent Developments and New Applications, Dec. 21, 2006, p. 115, Elsevier Science.
Extended European Search Report including Written Opinion for Application No. 19893049.7 dated Apr. 8, 2021, 11 pages.
Third Party Observation for PCT/KR2019/012832 submitted Apr. 6, 2021, 14 pages.

*Primary Examiner* — Brian A McCaig
(74) *Attorney, Agent, or Firm* — Lerner David LLP

(57) ABSTRACT

The present disclosure relates to a preparation method of a super absorbent polymer capable of preparing a super absorbent polymer exhibiting an improved absorption rate while reducing an amount of a blowing agent used. The preparation method of a super absorbent polymer includes: preparing a monomer mixture including a water-soluble ethylene-based unsaturated monomer having at least partially neutralized acidic groups and an internal cross-linking agent; adjusting a dynamic pressure applied to the monomer mixture being transferred to 140 Pa or more by controlling a transfer rate while transferring the monomer mixture to a polymerization reactor; cross-linking and polymerizing the monomer mixture transferred to the polymerization reactor to form a hydrogel polymer; drying, pulverizing and classifying the hydrogel polymer to form a base resin powder; and further cross-linking a surface of the base resin powder in the presence of a surface cross-linking agent to form a surface cross-linked layer.

15 Claims, No Drawings

(56) References Cited

U.S. PATENT DOCUMENTS

| | | | |
|---|---|---|---|
| 2014/0038817 A1 | 2/2014 | Kruger et al. | |
| 2014/0296465 A1 | 10/2014 | Sakamoto et al. | |
| 2015/0259494 A1 | 9/2015 | Takaai et al. | |
| 2015/0307667 A1* | 10/2015 | Wada | C08J 3/075 525/329.7 |
| 2016/0332141 A1 | 11/2016 | Machida et al. | |
| 2017/0066862 A1 | 3/2017 | Matsumoto et al. | |
| 2018/0257059 A1 | 9/2018 | Heo et al. | |
| 2019/0100629 A1 | 4/2019 | Nam et al. | |
| 2019/0307980 A1 | 10/2019 | Haibach et al. | |
| 2020/0009530 A1 | 1/2020 | Ahn et al. | |
| 2020/0164344 A1 | 5/2020 | Kim et al. | |

FOREIGN PATENT DOCUMENTS

| | | | |
|---|---|---|---|
| EP | 2342236 | B1 | 12/2012 |
| EP | 3318595 | A1 | 5/2018 |
| EP | 3406655 | A1 | 11/2018 |
| JP | H11005808 | A | 1/1999 |
| JP | 2004155963 | A | 6/2004 |
| JP | 2005162834 | A | 6/2005 |
| JP | 2006342306 | A | 12/2006 |
| JP | 2011526962 | A | 10/2011 |
| JP | 2019528821 | A | 10/2019 |
| KR | 20110138636 | A | 12/2011 |
| KR | 101627003 | B1 | 6/2016 |
| KR | 101630470 | B1 | 6/2016 |
| KR | 20170057705 | A | 5/2017 |
| KR | 20180087049 | A | 8/2018 |
| KR | 20180112110 | A | 10/2018 |
| WO | 1987003208 | A1 | 6/1987 |
| WO | 2010040466 | A1 | 4/2010 |
| WO | 2015133440 | A1 | 9/2015 |
| WO | 2018110757 | A1 | 6/2018 |
| WO | 2018117391 | A1 | 6/2018 |

* cited by examiner

PREPARATION METHOD OF SUPER ABSORBENT POLYMER

CROSS-REFERENCE TO RELATED APPLICATIONS

The present application is a national phase entry under 35 U.S.C. § 371 of International Application No. PCT/KR2019/012832, filed on Oct. 1, 2019, which claims priority to Korean Patent Application No. 10-2018-0157082 filed on Dec. 7, 2018, the disclosures of which are incorporated herein by reference in their entirety.

BACKGROUND OF THE INVENTION

(a) Field of the Invention

The present disclosure relates to a preparation method of a super absorbent polymer capable of preparing a super absorbent polymer exhibiting an improved absorption rate while reducing an amount of a blowing agent used.

(b) Description of the Related Art

A super absorbent polymer (SAP) is a type of synthetic polymeric material capable of absorbing 500 to 1000 times its own weight of moisture. Various manufacturers have denominated it with different names, such as SAM (Super Absorbency Material), AGM (Absorbent Gel Material), and the like. Such super absorbent polymers started to be practically applied in sanitary products, and they are now being widely used not only for hygiene products such as disposable diapers for children, etc., but also for water retaining soil products for gardening, water stop materials for the civil engineering and construction, sheets for raising seedling, fresh-keeping agents for food distribution fields, materials for poultices, or the like.

In most cases, these super absorbent polymers have been widely used in the field of hygienic materials such as diapers or sanitary napkins. In such hygienic materials, the super absorbent polymer is generally contained in a state of being spread in the pulp. In recent years, however, continuous efforts have been made to provide hygienic materials such as diapers having a thinner thickness. As a part of such efforts, the development of so-called pulpless diapers and the like in which the pulp content is reduced or pulp is not used at all is being actively advanced.

As described above, in the case of hygienic materials in which the pulp content is reduced or the pulp is not used, a super absorbent polymer is contained at a relatively high ratio and these super absorbent polymer particles are inevitably contained in multiple layers in the hygienic materials. In order for the whole super absorbent polymer particles contained in the multiple layers to absorb liquid such as urine more efficiently, it is necessary for the super absorbent polymer to basically exhibit high absorption performance and absorption rate.

Accordingly, in recent years, attempts have been made to manufacture and provide a super absorbent polymer exhibiting an improved absorption rate.

The most common method for increasing the absorption rate is a method of increasing the surface area of the super absorbent polymer by forming a porous structure inside the super absorbent polymer.

In order to increase the surface area of the super absorbent polymer, a method of forming a porous structure in the base resin powder by a cross-linking polymerization using a carbonate-based blowing agent has been conventionally applied. When using such a carbonate-based blowing agent, carbon dioxide gas may be generated in the polymerization process to form fine pores, so that a super absorbent polymer having a porous structure can be produced.

However, in this method, the effect of generating carbon dioxide gas is reduced depending on the polymerization temperature and time, and as a result, there is a disadvantage in that variation occurs between properties of the super absorbent polymer. In addition, when chemical foaming using the carbonate-based blowing agent is performed, a large amount of undesired fine powder is generated in the process such as drying and pulverization, thereby lowering other physical properties of the super absorbent polymer. In addition, there was a disadvantage in the process such as the need for recycling of fine powders.

Accordingly, there is a continuous demand for the development of a technology capable of preparing a super absorbent polymer exhibiting an improved absorption rate by forming an appropriate porous structure while reducing an amount of a blowing agent used.

SUMMARY OF THE INVENTION

Technical Problem

According to the present disclosure, there is provided a preparation method of a super absorbent polymer capable of preparing a super absorbent polymer exhibiting an improved absorption rate while reducing an amount of a blowing agent used.

Technical Solution

There is provided a preparation method of a super absorbent polymer, including the steps of:
preparing a monomer mixture including a water-soluble ethylene-based unsaturated monomer having at least partially neutralized acidic groups and an internal cross-linking agent;
adjusting a dynamic pressure applied to the monomer mixture being transferred calculated by the following Equation 1 to 0.140 kPa or more by controlling a transfer rate while transferring the monomer mixture to a polymerization reactor;
cross-linking and polymerizing the monomer mixture transferred to the polymerization reactor to form a hydrogel polymer;
drying, pulverizing and classifying the hydrogel polymer to form a base resin powder; and
further cross-linking a surface of the base resin powder in the presence of a surface cross-linking agent to form a surface cross-linked layer:

$$\text{Dynamic pressure} = \tfrac{1}{2} * p * V^2 \qquad \text{[Equation 1]}$$

in Equation 1, p denotes a density (g/cm$^3$) of the monomer mixture being transferred, and V denotes a transfer rate (m/s) of the monomer mixture.

Hereinafter, a preparation method of a super absorbent polymer according to a specific embodiment of the present invention will be described in detail. However, this is merely presented as an example of the present invention, and will be apparent to those skilled in the art that the scope of the present invention is not limited to these embodiments, and various modifications can be made to the embodiments within the scope of the present invention.

In addition, unless stated otherwise throughout this specification, the term "comprise" "include" or "contain" refers to including any constituent element (or constituent component) without particular limitation, and it cannot be interpreted as a meaning of excluding an addition of other constituent element (or constituent component).

According to one embodiment of the present disclosure, there is provided a preparation method of a super absorbent polymer, including the steps of:

preparing a monomer mixture including a water-soluble ethylene-based unsaturated monomer having at least partially neutralized acidic groups and an internal cross-linking agent;

adjusting a dynamic pressure applied to the monomer mixture being transferred calculated by the following Equation 1 to 0.140 kPa or more by controlling a transfer rate while transferring the monomer mixture to a polymerization reactor;

cross-linking and polymerizing the monomer mixture transferred to the polymerization reactor to form a hydrogel polymer;

drying, pulverizing and classifying the hydrogel polymer to form a base resin powder; and further cross-linking a surface of the base resin powder in the presence of a surface cross-linking agent to form a surface cross-linked layer:

Dynamic pressure=½*p*V²  [Equation 1]

in Equation 1, p denotes a density (g/cm³) of the monomer mixture being transferred, and V denotes a transfer rate (m/s) of the monomer mixture.

The present inventors continued to study to develop a technology capable of preparing a super absorbent polymer exhibiting a developed porous structure and an excellent absorption rate while reducing an amount of a blowing agent used.

As a result of the research of the present inventors, it has been found that when a dynamic pressure applied to the monomer mixture in a specific section of a transfer pipe is adjusted to 0.140 kPa or more, 0.150 to 1.000 kPa, or 0.150 to 0.800 kPa by changing a diameter of the transfer pipe or a transfer rate of the monomer mixture through the transfer pipe in the process of transferring the monomer mixture to a polymerization reactor, a super absorbent polymer exhibiting a developed porous structure and an excellent absorption rate could be prepared while reducing an amount of a blowing agent used by physical foaming. Thus, the present invention has been completed on the basis of such findings.

This may be because gas solubility such as oxygen in the monomer mixture decreases, as the pressure applied to the monomer mixture changes instantaneously during transfer through the transfer pipe. Therefore, oxygen bubbles are generated from the monomer mixture in the step of adjusting the dynamic pressure, and a foaming polymerization may proceed in the cross-linking polymerization step by the generated bubbles. As a result, a super absorbent polymer having a developed porous structure may be prepared by physical foaming even if a blowing agent is not used or its amount is reduced.

Since the super absorbent polymer uses a minimum amount of a blowing agent, it may exhibit an excellent absorption rate without a problem due to the blowing agent, and the deterioration in physical properties by the blowing agent may be reduced, thereby maintaining the remaining physical properties excellent. As a result, according to the method of one embodiment, it is possible to prepare a super absorbent polymer exhibiting an excellent absorption rate and various physical properties, while reducing the amount of the blowing agent used.

Hereinafter, a preparation method of one embodiment will be described in more detail in each step.

In the preparation method of a super absorbent polymer of one embodiment, a monomer mixture, which is a raw material of the super absorbent polymer, including an acrylic acid-based monomer having at least partially neutralized acidic groups, an internal cross-linking agent and a polymerization initiator, and optionally a blowing agent, is polymerized to form a hydrogel polymer, and then dried, pulverized and classified to form a base resin powder.

This will be described in more detail.

The monomer mixture, which is a raw material of the super absorbent polymer, includes a water-soluble ethylene-based unsaturated monomer having at least partially neutralized acidic groups, more specifically an acrylic acid-based monomer, and an internal cross-linking agent.

The acrylic acid-based monomer is a compound represented by the following Chemical Formula 1:

$R^1$—$COOM^1$  [Chemical Formula 1]

in Chemical Formula 1, $R^1$ is a C2 to C5 alkyl group having an unsaturated bond, and M 1 is a hydrogen atom, a monovalent or divalent metal, an ammonium group, or an organic amine salt.

Preferably, the acrylic acid-based monomer includes at least one selected from the group consisting of acrylic acid, methacrylic acid, and a monovalent metal salt, a divalent metal salt, an ammonium salt, and an organic amine salt thereof.

Herein, the acrylic acid-based monomers may be those having acidic groups which are at least partially neutralized. Preferably, the monomers may be those partially neutralized with an alkali substance such as sodium hydroxide, potassium hydroxide, ammonium hydroxide, or the like. In this regard, a degree of neutralization of the acrylic acid-based monomer may be 80 mol % or less, 40 to 75 mol %, or 50 to 70 mol %.

An excessively high degree of neutralization causes the neutralized monomers to be precipitated, and thus polymerization may not readily occur. Furthermore, the effect of additional neutralization after the initiation of surface cross-linking is substantially eliminated, so that a degree of cross-linking of the surface cross-linked layer is not optimized, and liquid permeability of the super absorbent polymer may not be sufficient. On the contrary, an excessively low degree of neutralization not only deteriorates the absorbency of the polymer, but also endows the polymer with hard-to-handle properties, such as those of an elastic rubber.

The concentration of the monomer may be 20 to 60 wt %, 30 to 55 wt %, or 40 to 50 wt % based on the monomer mixture including raw materials of the super absorbent polymer and a solvent, and properly controlled in consideration of polymerization time and reaction conditions. However, when the concentration of the monomer is excessively low, the yield of the super absorbent polymer may become low and economical efficiency may be reduced. On the contrary, when the concentration of the monomer is excessively high, there is a process problem that a part of the monomers is precipitated, or pulverization efficiency is lowered upon pulverization of the polymerized hydrogel polymer, and the physical properties of the super absorbent polymer may be deteriorated.

In the preparation method of a super absorbent polymer of one embodiment, a polymerization initiator that has been generally used for preparing a super absorbent polymer can be applied without particular limitations.

Specifically, the polymerization initiator may be an initiator for thermal polymerization or an initiator for photopolymerization by UV radiation according to the polymerization method. However, even when the photopolymerization method is applied thereto, a certain amount heat is generated by UV radiation and the like, and some heat occurs as the polymerization reaction, an exothermal reaction, progresses. Therefore, the composition may additionally include the thermal polymerization initiator.

Any compound which can form a radical by light such as UV rays may be used as the photopolymerization initiator without limitation.

For example, the photopolymerization initiator may be one or more compounds selected from the group consisting of benzoin ether, dialkyl acetophenone, hydroxyl alkylketone, phenyl glyoxylate, benzyl dimethyl ketal, acyl phosphine, and α-aminoketone. Further, as the specific example of acyl phosphine, commercial lucirin TPO, namely, 2,4,6-trimethyl-benzoyl-trimethyl phosphine oxide, may be used. More various photopolymerization initiators are well disclosed in "UV Coatings: Basics, Recent Developments and New Application (Elsevier, 2007)" written by Reinhold Schwalm, p 115, and the present invention is not limited thereto.

The concentration of the photopolymerization initiator in the monomer composition may be 0.01 to 1.0 wt %, 0.1 to 0.9 wt %, or 0.3 to 0.7 wt %. When the concentration of the photopolymerization initiator is excessively low, the polymerization rate becomes slow, and when the concentration of the photopolymerization initiator is excessively high, the molecular weight of the super absorbent polymer becomes low and the properties may be uneven.

Furthermore, as the thermal polymerization initiator, one or more initiators selected from the group consisting of a persulfate-based initiator, an azo-based initiator, hydrogen peroxide, and ascorbic acid may be used. Specifically, sodium persulfate ($Na_2S_2O_8$), potassium persulfate ($K_2S_2O_8$), ammonium persulfate (($NH_4$)$_2S_2O_8$), and the like may be used as examples of the persulfate-based initiators; and 2,2-azobis-(2-amidinopropane)dihydrochloride, 2,2-azobis-(N,N-dimethylene)isobutyramidinedihydrochloride, 2-(carbamoylazo)isobutylonitril, 2,2-azobis-[2-(2-imidazolin-2-yl)propane]dihydrochloride, 4,4-azobis-(4-cyanovaleric acid), and the like may be used as examples of azo-based initiators. More various thermal polymerization initiators are well disclosed in "Principle of Polymerization (Wiley, 1981)" written by Odian, p 203, and the present invention is not limited thereto.

According to one embodiment of the present disclosure, the monomer mixture includes an internal cross-linking agent as a raw material of the super absorbent polymer. The internal cross-linking agent is used for cross-linking the interior of a polymer in which an acrylic acid-based monomer is polymerized, that is, a base resin, and is different from the surface cross-linking agent for cross-linking the surface of the polymer.

The kind of the internal cross-linking agent is not particularly limited, and any internal cross-linking agent that has been generally used for preparing a super absorbent polymer can be applied without particular limitations. Specific examples of the internal cross-linking agent include poly(meth)acrylate-based compounds of a C2 to C20 polyol, polyglycidyl ether-based compounds of a C2 to C20 polyol, allyl (meth)acrylate-based compounds having 2 to 20 carbon atoms, and the like.

More specific examples of the internal cross-linking agent include trimethylolpropane tri(meth)acrylate, ethyleneglycol di(meth)acrylate, polyethyleneglycol di(meth)acrylate, propyleneglycol di(meth)acrylate, polypropyleneglycol di(meth)acrylate, butanediol di(meth)acrylate, butyleneglycol di(meth)acrylate, diethyleneglycol di(meth)acrylate, hexanediol di(meth)acrylate, triethyleneglycol di(meth)acrylate, tripropyleneglycol di(meth)acrylate, tetraethyleneglycol di(meth)acrylate, dipentaerythritol pentaacrylate, glycerin tri(meth)acrylate, pentaerythritol tetraacrylate, ethyleneglycol diglycidyl ether, polyethyleneglycol diglycidyl ether, glycerol polyglycidyl ether, propyleneglycol diglycidyl ether, polypropyleneglycol diglycidyl ether, and the like, and various other polyfunctional compounds can be used as the internal cross-linking agent.

The internal cross-linking agent is included in a concentration of 0.01 to 1 wt %, 0.05 to 0.8 wt %, or 0.2 to 0.7 wt % based on the monomer mixture, thereby forming a cross-linking structure inside the hydrogel polymer and the base resin powder formed therefrom. When the internal cross-linking agent is included in an excessively small amount, the degree of internal cross-linking of the super absorbent polymer may be lowered, and thus various physical properties such as absorbency under pressure may be deteriorated. Conversely, when the internal cross-linking agent is included in an excessively large amount, absorption performance such as water retention capacity may be deteriorated.

Meanwhile, the above-described monomer mixture may include a blowing agent in an amount of 0.01 to 0.3 wt %, 0.05 to 0.25 wt %, or 0.1 to 0.2 wt % based on the total monomer mixture, if necessary, depending on the absorption rate to achieve. However, in the method of one embodiment, it is possible to use a greatly reduced amount of the blowing agent than previously known to obtain the same level of porosity, thus problems due to the excessive use of the blowing agent may be minimized.

As the blowing agent, any blowing agent that has been generally used for a foaming polymerization of a super absorbent polymer can be used. For example, a carbonate-based blowing agent may be used. Specific examples of the carbonate-based blowing agent include sodium bicarbonate, sodium carbonate, potassium bicarbonate, potassium carbonate, calcium bicarbonate, calcium carbonate, magnesium bicarbonate) and magnesium carbonate.

The monomer composition may further include an additive such as a thickener, a plasticizer, a preservation stabilizer, an antioxidant, and the like, if necessary.

The raw materials such as the monomer having at least partially neutralized acidic groups, the photopolymerization initiator, the thermal polymerization initiator, the internal cross-linking agent, the optional blowing agent, and the additive may be prepared in the form of a solution dissolved in a solvent.

At this time, any solvent which can dissolve the components may be used without limitation, and for example, one or more solvents selected from water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butyrolactone, carbitol, methylcellosolve acetate, and N,N-dimethylacetamide may be used.

The solvent may be included in the monomer composition at a residual quantity excluding the above components.

After forming the monomer mixture by the above-described method, a dynamic pressure applied to the monomer mixture being transferred calculated by the Equation 1 may be adjusted to 0.140 kPa or more, 0.150 to 1.000 kPa, or 0.150 to 0.800 kPa, by controlling a transfer rate thereof while transferring the monomer mixture to a polymerization reactor through a transfer pipe.

As described above, gas solubility such as oxygen in the monomer mixture may be reduced by changing a diameter of the transfer pipe or a transfer rate during the transfer of the monomer mixture to adjust the dynamic pressure applied to the monomer mixture. Therefore, oxygen bubbles are generated from the monomer mixture, and a foaming polymerization may proceed in the cross-linking polymerization step by the generated bubbles, thereby preparing a super absorbent polymer having a developed porous structure by physical foaming.

When the dynamic pressure is too low, the physical foaming and foaming polymerization may not proceed properly, and thus the porous structure and absorption rate of the super absorbent polymer may not be properly achieved. Conversely, when the dynamic pressure is excessively high, not only the additional foaming effect is not large, but also the transfer rate during the process is not properly controlled, which may cause difficulties in the process.

The dynamic pressure can be calculated from a density and a transfer rate of the monomer mixture, as confirmed in the Equation 1, and the density of the monomer mixture can be easily measured and calculated by those skilled in the art using the concentration or type of each component. The density of the monomer mixture may generally be determined by using a pycnometer, a hydrometer or a density layer. The most common method is a method by using a hydrometer.

Meanwhile, it is possible to control the dynamic pressure described above by changing the diameter of the transfer pipe or the transfer rate of the monomer mixture. For example, the monomer mixture is transferred along a transfer pipe having a diameter that varies from section to section, and specifically, the diameter of the transfer pipe may be reduced along the transfer path. As a result, the monomer mixture may be controlled to have a maximum transfer rate in the minimum diameter section of the transfer pipe, and the above-described dynamic pressure may be achieved by changing the diameter of the transfer pipe or the transfer rate of the monomer mixture.

In a more specific example, the transfer pipe may have a diameter of 0.002 to 0.01 m, or 0.005 to 0.009 m in the minimum diameter section, and have a diameter of 0.011 to 0.020 m, or 0.012 to 0.015 m in the maximum diameter section before the minimum diameter section. The diameter of the transfer pipe may be appropriately determined within the above-mentioned range in consideration of the flow rate of the monomer mixture for achieving proper productivity of the super absorbent polymer, the transfer rate for achieving the dynamic pressure described above, and the like.

In addition, the monomer mixture may be transferred in the minimum diameter section of the transfer pipe at a rate of 0.45 to 2.5 m/s, or 0.7 to 2.0 m/s, and transferred in the maximum diameter section of the transfer pipe at a rate of 0.1 to 0.5 m/s, or 0.2 to 0.4 m/s.

In the preparation of a super absorbent polymer, the monomer mixture may be transferred through the transfer pipe at a flow rate of 100 to 15000 kg/hr, 100 to 13000 kg/hr, or 110 to 1000 kg/hr in order to achieve proper productivity.

When transferring the monomer mixture at such a flow rate, the dynamic pressure applied to the monomer mixture can be adjusted to the above-described range by changing the diameter of the transfer pipe and/or the transfer rate of the monomer mixture within the above-described range. As a result, it is possible to manufacture a super absorbent polymer exhibiting a developed porous structure and an excellent absorption rate by optimizing the degree of physical foaming.

After transferring to the polymerization reactor while physically foaming the monomer mixture by the above-described method, the monomer mixture may be thermally polymerized or photopolymerized to form a hydrogel polymer. The methods/conditions of the polymerization step are not particularly limited, and may be in accordance with the general polymerization conditions and methods of a super absorbent polymer.

Specifically, the polymerization method is largely divided into thermal polymerization and photopolymerization according to an energy source of the polymerization. In the case of thermal polymerization, it is generally carried out in a reactor having an agitation spindle, such as a kneader. In the case of photopolymerization, it may be carried out in a reactor equipped with a movable conveyor belt. However, the polymerization method is just an example, and the present invention is not limited thereto.

For example, in the reactor equipped with an agitation spindle such as a kneader, the hydrogel polymer obtained by thermal polymerization by supplying hot air or heating the reactor may be discharged to a reactor outlet in the form of several centimeters to several millimeters depending on a shape of the agitation spindle provided in the reactor. Specifically, a size of the hydrogel polymer obtained may vary depending on the concentration and injection rate of the monomer mixture to be injected, and a hydrogel polymer having a weight average particle diameter of 2 to 50 mm or 3 to 30 mm may be usually obtained.

In addition, when photopolymerization is performed in the reactor equipped with a movable conveyor belt as described above, a hydrogel polymer in the form of a sheet having a belt width may usually be obtained. At this time, a thickness of the polymer sheet may vary depending on the concentration and injection rate of the monomer mixture to be injected, and it is preferable to supply the monomer mixture so that the polymer in the form of a sheet has a thickness of 0.5 to 5 cm, or 1 to 3 cm. When the monomer mixture is supplied to such an extent that the thickness of the polymer sheet is too thin, the production efficiency may be low. When the thickness of the polymer sheet exceeds 5 cm, the polymerization reaction may not occur evenly over the entire thickness due to the excessively thick thickness.

Generally, the moisture content of the hydrogel polymer obtained by the above method may be 40 to 80 wt %, or 50 to 70 wt %. At this time, "moisture content" in the present description is the content of moisture in the entire weight of the hydrogel polymer, and it means a value of which the weight of the dried polymer is subtracted from the weight of the hydrogel polymer. Specifically, the moisture content is defined as a value calculated from the weight loss due to moisture evaporation from the polymer in the process of increasing the temperature of the polymer and drying the same through infrared heating. At this time, the drying condition for measuring the moisture content is that the temperature is increased to 180° C. and maintained at 180°

C., and the total drying time is 20 min including 5 min of a heating step.

Subsequently, the hydrogel polymer is dried.

Herein, a coarse pulverizing step may be further included before the drying step for increasing the drying efficiency, if necessary.

The pulverizing machine used is not particularly limited. Specifically, it may include at least one selected from the group consisting of a vertical pulverizer, a turbo cutter, a turbo grinder, a rotary cutter mill, a cutter mill, a disc mill, a shred crusher, a crusher, a chopper, and a disc cutter, but it is not limited thereto.

In the pulverizing step, the hydrogel polymer may be crushed to have a diameter of 2 to 50 mm, or 3 to 30 mm. The diameter of the hydrogel polymer may be defined as the longest distance among linear distances connecting arbitrary points on the surface of the hydrogel polymer.

It is technically difficult to pulverize the hydrogel polymer to have a diameter of less than 2 mm because of its high moisture content, and there may be a phenomenon that the crushed particles cohere with each other. Meanwhile, when the polymer is crushed to have a diameter of larger than 50 mm, the efficiency enhancing effect in the subsequent drying step may be low.

The hydrogel polymer pulverized as above or the hydrogel polymer immediately after the polymerization without the pulverizing step is subjected to drying. At this time, the drying temperature of the drying step may be 150 to 250° C. When the drying temperature is lower than 150° C., the drying time may become excessively long and the properties of the super absorbent polymer finally prepared may decrease. And when the drying temperature is higher than 250° C., the surface of the polymer is excessively dried to generate fine powders in a subsequent pulverizing process, and the properties of the super absorbent polymer finally prepared may decrease. Therefore, the drying process may be preferably carried out at a temperature of 150 to 200° C., more preferably at a temperature of 160 to 180° C.

Furthermore, the drying time may be 10 to 90 minutes, or 20 to 70 minutes in consideration of process efficiency, but it is not limited thereto.

The drying method in the drying step is not particularly limited if it has been generally used in the drying process of the hydrogel polymer. Specifically, the drying step may be carried out by the method of hot air provision, infrared radiation, microwave radiation, UV ray radiation, and the like. The moisture content of the polymer after the drying step may be 0.1 to 10 wt %, or 1 to 8 wt %. When the moisture content after drying is too low, the hydrogel polymer may be deteriorated during the drying process, thereby degrading physical properties of the super absorbent polymer. Conversely, when the moisture content is too high, absorption performance may be reduced due to the large amount of moisture in the super absorbent polymer, or it may be difficult to perform subsequent processes.

Subsequently, a step of pulverizing the dried polymer obtained from the drying step is carried out.

The polymer powder obtained after the pulverization step may have a diameter of 150 to 850 μm. In order to pulverize the polymer into such diameter, a pin mill, a hammer mill, a screw mill, a roll mill, a disc mill, or a jog mill may be used as the pulverizer, but it is not limited thereto.

Further, in order to control the properties of the super absorbent polymer powder which is finally commercialized after the pulverization step, a separate process of classifying the polymer powders obtained after the pulverization according to the particle diameter may be carried out. The polymer powders may be classified to have a constant weight ratio according to the particle diameter.

After obtaining the base resin in the powder form through the above-described classification step, the base resin is heated in the presence of a surface cross-linking agent to carry out surface cross-linking.

In the general preparation method of a super absorbent polymer, a surface cross-linking solution containing a surface cross-linking agent is mixed with a dried, pulverized and classified polymer, that is, a base resin powder, and then the mixture is heated to carry out a surface cross-linking reaction of the base resin powder.

The surface cross-linking step is a step of inducing a cross-linking reaction on the surface of the pulverized polymer in the presence of a surface cross-linking agent to form a super absorbent polymer having improved physical properties. Through the surface cross-linking, a surface cross-linked layer is formed on the surface of the pulverized and classified base resin powder.

Generally, surface cross-linking agents are applied on the surface of the base resin powder, so that surface cross-linking reactions occur on the surface of the base resin powder, which improves cross-linkability on the surface of the particles without substantially affecting the interior of the particles. Therefore, the surface cross-linked super absorbent polymer particles have a higher degree of cross-linking near the surface than in the interior, as the cross-linked polymer on the surface of the base resin powder is further cross-linked.

Meanwhile, the surface cross-linking agent is a compound capable of reacting with functional groups of the base resin. For example, polyalcohol-based compounds, polyepoxy-based compounds, polyamine compounds, haloepoxy compounds, condensates of haloepoxy compounds, oxazoline-based compounds, or alkylene carbonate compounds may be used without particular limitations.

Specific examples of the polyalcohol-based compound may include one or more selected from the group consisting of di-, tri-, tetra- or polyethylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexane dimethanol.

Further, the polyepoxy-based compound may include ethylene glycol diglycidyl ether, glycidol or the like. The polyamine compound may include one or more selected from the group consisting of ethylene diamine, diethylene triamine, triethylene tetraamine, tetraethylene pentamine, pentaethylene hexamine, polyethylene imine, and polyamide polyamine.

Further, the haloepoxy compound may include epichlorohydrin, epibromohydrin, or α-methylephichlorohydrin. Meanwhile, the mono-, di-, or polyoxazolidinone compound may include, for example, 2-oxazolidinone or the like.

Further, the alkylene carbonate-based compound may include ethylene carbonate, propylene carbonate, or the like. These may be used alone or in combination with each other.

The amount of the surface cross-linking agent added may be appropriately selected depending on the kind of the surface cross-linking agent added or the reaction conditions. However, the surface cross-linking agent may be generally used in an amount of 0.001 to 5 parts by weight, 0.01 to 3 parts by weight, or 0.05 to 2 parts by weight based on 100 parts by weight of the base resin powder.

When the amount of the surface cross-linking agent is excessively small, the surface cross-linking reaction hardly occurs, and when the amount is higher than 5 parts by weight based on 100 parts by weight of the polymer, absorbency such as water retention capacity may be deteriorated due to the excessive surface cross-linking reaction.

When the surface cross-linking agent is added, water may be further mixed together and added in the form of a surface cross-linking solution. When water is added, there is an advantage that the surface cross-linking agent can be uniformly dispersed in the polymer. Herein, the added amount of water is preferably 1 to 10 parts by weight based on 100 parts by weight of the polymer in order to optimize a surface penetration depth of the surface cross-linking agent, while inducing even dispersion of the surface cross-linking agent and preventing the polymer powder from aggregating.

Meanwhile, the above-mentioned surface cross-linking step may further use at least one selected from the group consisting of polyvalent metal salts, for example, aluminum salts, more specifically, sulfates, potassium salts, ammonium salts, sodium salts, and hydrochloride salts of aluminum, in addition to the surface cross-linking agent.

As the polyvalent metal salt is additionally used, liquid permeability of the super absorbent polymer prepared by the method of one embodiment may be further improved. The polyvalent metal salt may be added to the surface cross-linking solution together with the surface cross-linking agent, and may be used in an amount of 0.01 to 4 parts by weight based on 100 parts by weight of the base resin powder.

Meanwhile, the base resin powder is subjected to the surface cross-linking by heating the mixture of the base resin powder and the surface cross-linking solution.

The surface cross-linking step may be carried out under well-known conditions depending on the kind of the surface cross-linking agent, for example, at a temperature of 100 to 200° C. for 20 to 60 minutes. In a more specific example, the surface cross-linking step may be carried out by adding a surface cross-linking agent, and the like to the base resin powder having an initial temperature of 20° C. to 80° C., increasing the temperature to a maximum temperature of 140° C. to 200° C. over 10 minutes to 30 minutes, and maintaining the maximum temperature for 5 to 60 minutes for heat-treatment.

Depending on the surface cross-linking conditions, basic absorption characteristics such as water retention capacity of the super absorbent polymer, and liquid permeability and/or absorbency under pressure may be optimized together.

The heating means for the surface cross-linking reaction is not particularly limited. It is possible to provide a thermal media thereto or provide a heat source directly thereto. At this time, usable thermal media may be a heated fluid such as steam, hot air, hot oil, and the like, but the present invention is not limited thereto. Furthermore, the temperature of the thermal media provided thereto may be properly selected in consideration of the means of the thermal media, heating speed, and target temperature of heating. Meanwhile, an electric heater or a gas heater may be used as the heat source provided directly, but the present invention is not limited thereto.

The super absorbent polymer prepared by the above-described method includes a base resin powder containing a first cross-linked polymer of a water-soluble ethylene-based unsaturated monomer having at least partially neutralized acidic groups; and a surface cross-linked layer in which the first cross-linked polymer is additionally cross-linked by a surface cross-linking agent on the base resin powder, and a plurality of pores are formed in the base resin powder.

The super absorbent polymer substantially does not contain a blowing agent, and may exhibit an excellent absorption rate.

More specifically, the super absorbent polymer may have T-20 of 170 seconds or less, 165 seconds or less, or 163 seconds or less, and 100 seconds or more, 110 seconds or more, or 120 seconds or more, which represents the time required for 1 g of the polymer to absorb 20 g of an aqueous solution of sodium chloride and C12 to C14 alcohol ethoxylate under a pressure of 0.3 psi. This may mean the high absorption rate of the super absorbent polymer.

In addition, the super absorbent polymer may have centrifuge retention capacity (CRC) to saline (0.9 wt % aqueous solution of sodium chloride) for 30 min of 28 g/g or more, or 28.4 g/g or more, and 40 g/g or less, 36 g/g or less, or 34 g/g or less, measured according to the EDANA method WSP 241.3.

In addition, the super absorbent polymer may have absorbency under pressure (AUP) at 0.7 psi of 23 to 27 g/g, 23.5 to 26.5 g/g, or 24 to 26 g/g, measured according to the EDANA method WSP 242.3-10. The absorbency under pressure may mean the excellent absorbency under pressure of the super absorbent polymer.

In addition, the super absorbent polymer of one embodiment may have saline (0.685 wt % aqueous solution of sodium chloride) flow conductivity (SFC, $10^{-7}$ $cm^3 \cdot s/g$) of 30 ($\cdot 10^{-7}$ $cm^3 \cdot s/g$) or more, or 35($\cdot 10^{-7}$ $cm^3 \cdot s/g$) or more, and 100($\cdot 10^{-7}$ $cm^3 \cdot s/g$) or less, or 70($\cdot 10^{-7}$ $cm^3 \cdot s/g$) or less.

The saline flow conductivity (SFC) can be measured and calculated according to methods well known to those skilled in the art, for example, the method disclosed in U.S. Pat. No. 5,562,646 at columns 54 to 59.

Since the super absorbent polymer prepared by the method of one embodiment is less deteriorated in other physical properties due to minimal use of a blowing agent, it can simultaneously exhibit an excellent absorption rate, excellent liquid permeability, water retention capacity and absorption capacity.

In addition, the super absorbent polymer may have a vortex time (absorption rate) of 5 to 50 seconds, or 10 to 45 seconds by a vortex method. This can also mean the excellent absorption rate of the super absorbent polymer.

As described above, the super absorbent polymer obtained according to the method of one embodiment exhibits an excellent absorption rate, and an excessive use of a blowing agent is not required, thereby maintaining other various physical properties excellent. As a result, the super absorbent polymer can be suitably used in sanitary materials such as diapers, in particular, ultra-thin sanitary materials having a reduced pulp content.

Advantageous Effects

As described above, according to the present disclosure, a super absorbent polymer exhibiting a developed porous structure by physical foaming and excellent absorption rate can be prepared only with minimal use of a blowing agent.

Therefore, the super absorbent polymer prepared by the above method exhibits an excellent absorption rate, and it is not necessary to use an excessive amount of a blowing agent, thereby maintaining other various physical properties such as absorption capacity and liquid permeability excellent. As a result, the super absorbent polymer can be suitably used in sanitary materials such as diapers, in particular, ultra-thin sanitary materials having a reduced pulp content.

DETAILED DESCRIPTION OF THE EMBODIMENTS

Hereinafter, the present invention will be described in more detail with reference to examples. However, these examples are for illustrative purposes only, and the invention is not intended to be limited by these examples.

Example 1

A monomer aqueous solution having a degree of neutralization of acrylic acid of 70 mol % and a monomer concentration of 43 wt % was prepared, in which the monomer aqueous solution includes acrylic acid, sodium hydroxide, polyethyleneglycol diacrylate (Mw=523; 0.5 wt % based on acrylic acid) as an internal cross-linking agent, and 0.033 g of diphenyl(2,4,6-trimethylbenzoyl)-phosphine oxide as a UV initiator.

Then, 0.3 wt % (based on monomer aqueous solution) of a blowing agent solution of 0.17 wt % of sodium hydrogen carbonate was mixed with the monomer aqueous solution, and the composition was first introduced through a single tube having a diameter (maximum diameter section) of 0.015 m at a flow rate of 110 kg/h. Secondarily, it was continuously transferred through a single tube (minimum diameter section) in which the diameter is changed to 0.008 m. Through this transfer, the monomer aqueous solution was introduced into a polymerization reactor equipped with a movable conveyor belt, and UV polymerization was performed for 2 minutes by irradiating ultraviolet rays (irradiation amount: 2 mW/cm$^2$) through a UV irradiation device to prepare a hydrogel polymer.

At this time, the dynamic pressure of the monomer aqueous solution composition passing through the final secondary single tube was 0.152 kPa.

After transferring the hydrogel polymer to a cutter, it was cut to a maximum length of 0.2 cm. At this time, the moisture content of the cut hydrogel polymer was 52 wt %.

Subsequently, the hydrogel polymer was dried for 30 minutes in a hot air dryer at a temperature of 190° C., and the dried hydrogel polymer was pulverized with a pin mill. Then, it was classified with a sieve to a polymer having a particle diameter of less than 150 μm and a polymer having a particle diameter of 150 μm to 850 μm.

Thereafter, the surface of the super absorbent polymer was treated by spraying an aqueous solution of surface cross-linking agent containing 1.5 parts by weight of ethylene carbonate based on 100 parts by weight of the prepared base resin powder. In addition, in the step of treating the surface, the classified base resin powder was supplied to a surface cross-linking reactor, and a surface cross-linking reaction was performed at a temperature of 190° C. or higher for 35 minutes.

After the surface treatment, the temperature of the super absorbent polymer was cooled to 90° C., and a surface treated super absorbent polymer having a particle diameter of 150 to 850 μm was obtained using a sieve. The fine powder having a particle diameter of less than 150 μm was contained in the super absorbent polymer in less than 2 wt %.

Example 2

It was carried out in the same manner as in Example 1, except that the transfer rate of the monomer aqueous solution was adjusted as shown in Table 1 below by adjusting the flow rate of the monomer aqueous solution composition to 150 kg/h, and the dynamic pressure of the monomer aqueous solution passing through the secondary single tube (minimum diameter section) was 0.282 kPa.

Example 3

It was carried out in the same manner as in Example 1, except that the transfer rate of the monomer aqueous solution was adjusted as shown in Table 1 below by adjusting the flow rate of the monomer aqueous solution composition to 242 kg/h, and the dynamic pressure of the monomer aqueous solution passing through the secondary single tube (minimum diameter section) was 0.734 kPa.

Comparative Example 1

It was carried out in the same manner as in Example 1, except that the transfer rate of the monomer aqueous solution was adjusted as shown in Table 1 below by adjusting the flow rate of the monomer aqueous solution composition to 90 kg/h, and the dynamic pressure of the monomer aqueous solution passing through the secondary single tube (minimum diameter section) was 0.101 kPa.

Comparative Example 2

It was carried out in the same manner as in Example 1, except that the flow rate of the monomer aqueous solution composition was adjusted to 242 kg/h, and the monomer aqueous solution was transferred without changing the diameter of the transfer pipe (single tube). At this time, the dynamic pressure of the monomer aqueous solution was 0.059 kPa.

Experimental Examples

The properties of each super absorbent polymer prepared in Examples and Comparative Examples, and various factors in the manufacturing process were measured and evaluated in the following manner.

(1) Density of Monomer Aqueous Solution

The density of the monomer mixture immediately before being transferred through a transfer pipe was measured by a method using a hydrometer from Mettler Toledo. As a result of the measurement, it was confirmed that the monomer aqueous solution prepared in Examples and Comparative Examples had a density of 1.05 g/cm$^3$.

(2) Transfer Rate of Monomer Aqueous Solution (m/s)

The transfer rate of the monomer aqueous solution was calculated from the following equation by obtaining a cross-sectional area from a diameter of the transfer pipe in the transfer section and measuring a flow rate of the monomer mixture in the same section:

$$\text{Transfer rate (m/s)} = \text{flow rate (m}^3/\text{hr)}/\text{cross-sectional area (m}^2)$$

(3) Dynamic Pressure (Pa)

The density and the transfer rate measured in (1) and (2) above were substituted into Equation 1 to calculate the dynamic pressure during transfer of the monomer aqueous solution.

(4) Particle Diameter Evaluation

The particle diameters of the base resin powder and the super absorbent polymer used in Examples and Comparative Examples were measured according to the EDANA (European Disposables and Nonwovens Association) WSP 220.3 method.

(5) Centrifuge Retention Capacity (CRC)

The centrifuge retention capacity (CRC) by absorption ratio under a non-loading condition was measured according to the EDANA (European Disposables and Nonwovens Association) WSP 241.3 method. After inserting $W_0$ (g, about 0.2 g) of the super absorbent polymer (or base resin powder) uniformly in a nonwoven fabric envelope and sealing the same, it was soaked in saline (0.9 wt % aqueous solution of sodium chloride) at room temperature. After 30 min, the envelope was centrifuged at 250 G for 3 minutes to drain, and the weight $W_2$ (g) of the envelope was measured. Further, after carrying out the same operation without using the super absorbent polymer, the weight $W_1$ (g) of the envelope was measured. Then, CRC (g/g) was calculated by using the obtained weight values according to the following Equation 2, and the water retention capacity was confirmed.

$$CRC(g/g)=\{[W_2(g)-W_1(g)-W_0(g)]/W_0(g)\} \quad \text{[Equation 2]}$$

(6) Absorbency Under Pressure (AUP)

The absorbency under pressure (AUP) of each super absorbent polymer prepared in Examples and Comparative Examples was measured according to the EDANA (European Disposables and Nonwovens Association) WSP 242.3-10 method.

First, a 400 mesh stainless steel screen was installed in a cylindrical bottom of a plastic having an inner diameter of 60 mm. $W_0$ (g, 0.90 g) of the polymer prepared in each of Examples and Comparative Examples was uniformly scattered on the screen at a temperature of 23±2° C. and a relative humidity of 45%. Thereafter, a piston which can uniformly provide a load of 4.83 kPa (0.7 psi) was placed on the polymer. Herein, the outer diameter of the piston was slightly smaller than 60 mm, there was no gap with the inner wall of the cylinder, and jig-jog of the cylinder was not interrupted. At this time, the weight $W_3$ (g) of the device was measured.

Subsequently, a glass filter having a diameter of 125 mm and a thickness of 5 mm was placed in a petri dish having a diameter of 150 mm, and saline (0.9 wt % sodium chloride) was poured in the dish. At this time, the saline was poured until the surface level of the saline became equal to the upper surface of the glass filter. After the measuring device was mounted on the glass filter, the liquid was absorbed for 1 hour under a load. After 1 hour, the measuring device was lifted, and the weight $W_4$ (g) was measured.

Then, AUP (g/g) was calculated by using the obtained weight values according to the following Equation 3.

$$AUP(g/g)=[W_4(g)-W_3(g)]/W_0(g) \quad \text{[Equation 3]}$$

In Equation 3, $W_0$ (g) is an initial weight (g) of the super absorbent polymer, $W_3$ (g) is a sum of a weight of the super absorbent polymer and a weight of the device providing a load to the polymer, and $W_4$ (g) is a sum of a weight of the super absorbent polymer and a weight of the device providing a load to the polymer, after making the super absorbent polymer absorb the saline for one hour under a load (0.7 psi).

(7) Saline Flow Conductivity (SFC)

The saline flow conductivity was measured and calculated according to the method disclosed in U.S. Pat. No. 5,562,646 at columns 54 to 59. It was measured in the same manner as the above US patent, except that the amount of the super absorbent polymer used in the measurement was changed to 1.5 g instead of 0.9 g.

(8) T-20

An aqueous solution in which 9 g of sodium chloride and 0.1 g of Lorodac (main component: C12 to C14 alcohol ethoxylate, CAS #68439-50-9) were dissolved in 1 L of distilled water was prepared, and the time required for 1 g of the super absorbent polymer to absorb 20 g of the aqueous solution under a pressure of 0.3 psi was calculated and measured. The specific measuring method of T-20 is disclosed in U.S. Patent Publication No. 2013-007940.

(9) Absorption Rate (Vortex Time)

The absorption rate (vortex time) of each super absorbent polymer of Examples and Comparative Examples was measured in seconds according to the method disclosed in International Patent Publication No. 1987-003208.

Specifically, the absorption rate (or vortex time) was calculated by adding 2 g of the super absorbent polymer to 50 mL of saline at 23° C. to 24° C., stirring a magnetic bar (8 mm in diameter and 31.8 mm in length) at 600 rpm, and measuring the time until vortex disappeared in seconds.

The results of the above properties are summarized in Table 1 below.

TABLE 1

| | Example 1 | Example 2 | Example 3 | Comp. Ex. 1 | Comp. Ex. 2 |
|---|---|---|---|---|---|
| Flow rate (kg/hr) | 110 | 150 | 242 | 90 | 242 |
| Pipe 1 Dia. (m) (Dia. in maximum diameter) | 0.015 | 0.015 | 0.015 | 0.015 | 0.015 |
| Transfer rate in maximum diameter section (m/s) | 0.31 | 0.31 | 0.31 | 0.31 | 0.31 |
| Pipe 2 Dia. (m) (Dia. in minimum diameter section) | 0.008 | 0.008 | 0.008 | 0.008 | 0.015 |
| Transfer rate in minimum diameter section (m/s) | 0.5 | 0.68 | 1.10 | 0.41 | 0.31 |
| Dynamic pressure (Pa) | 152 | 282 | 734 | 101 | 59 |
| CRC before surface crosslinking (base resin powder; g/g) | 36.5 | 36.2 | 36.5 | 35.8 | 36.1 |
| Properties after surface crosslinking | | | | | |
| CRC (g/g) | 29.1 | 29 | 28.4 | 28.6 | 29.3 |
| AUP (g/g) | 25.1 | 25 | 25.3 | 25.1 | 24.9 |
| SFC (1.5 g) | 35 | 36 | 35 | 33 | 32 |
| T20 (sec) | 163 | 153 | 120 | 180 | 210 |
| Vortex (sec) | 45 | 43 | 40 | 58 | 70 |

Referring to Table 1, it was confirmed that the super absorbent polymers prepared in Examples 1 to 3 in which a dynamic pressure of 0.140 kPa or more was applied during the transfer of the monomer aqueous solution had an improved absorption rate, while exhibiting water retention capacity, absorbency under pressure, and liquid permeability equivalent to or higher than those of Comparative Examples.

What is claimed is:

1. A preparation method of a super absorbent polymer, comprising:
   preparing a monomer mixture comprising a water-soluble ethylene-based unsaturated monomer having at least partially neutralized acidic groups and an internal cross-linking agent;
   transferring the monomer mixture to a polymerization reactor;
   during the transferring the monomer mixture to the polymerization reactor, adjusting a dynamic pressure applied to the monomer mixture being transferred calculated by the following Equation 1 to 0.140 kPa or more by controlling a transfer rate;
   cross-linking and polymerizing the monomer mixture transferred to the polymerization reactor to form a hydrogel polymer;
   drying, pulverizing and classifying the hydrogel polymer to form a base resin powder; and
   further cross-linking a surface of the base resin powder in the presence of a surface cross-linking agent to form a surface cross-linked layer:

$$\text{Dynamic pressure} = \tfrac{1}{2} * p * V^2 \qquad \text{[Equation 1]}$$

in Equation 1, p denotes a density (g/cm$^3$) of the monomer mixture being transferred, and V denotes a transfer rate (m/s) of the monomer mixture.

2. The preparation method of a super absorbent polymer of claim 1,
   wherein the monomer mixture is transferred along a transfer pipe having a diameter that varies from section to section, the monomer mixture has a maximum transfer rate in a minimum diameter section of the transfer pipe, and the dynamic pressure applied to the monomer mixture in the maximum transfer rate section is adjusted to 0.140 kPa or more.

3. The preparation method of a super absorbent polymer of claim 2,
   wherein the transfer pipe has a diameter of 0.002 to 0.01 m in the minimum diameter section, and has a diameter of 0.011 to 0.020 m in a maximum diameter section before the minimum diameter section.

4. The preparation method of a super absorbent polymer of claim 3,
   wherein the monomer mixture is transferred through the transfer pipe at a flow rate of 100 to 15000 kg/hr.

5. The preparation method of a super absorbent polymer of claim 2,
   wherein the monomer mixture is transferred in the minimum diameter section of the transfer pipe at a rate of 0.45 to 2.5 m/s, and is transferred in a maximum diameter section of the transfer pipe at a rate of 0.1 to 0.4 m/s.

6. The preparation method of a super absorbent polymer of claim 1,
   wherein the monomer mixture further comprises a blowing agent in an amount of 0.01 to 0.3 wt % based on a total mixture weight.

7. The preparation method of a super absorbent polymer of claim 1,
   wherein oxygen bubbles are generated in the monomer mixture during the dynamic pressure adjustment, and a foaming polymerization proceeds by the generated bubbles in the cross-linking polymerization.

8. The preparation method of a super absorbent polymer of claim 1,
   wherein the super absorbent polymer has T-20 of 170 seconds or less, wherein T-20 represents a time required for 1 g of the super absorbent polymer to absorb 20 g of an aqueous solution of sodium chloride and C12 to C14 alcohol ethoxylate under a pressure of 0.3 psi.

9. The preparation method of a super absorbent polymer of claim 1,
   wherein the super absorbent polymer has a centrifuge retention capacity (CRC) of saline (0.9 wt % aqueous solution of sodium chloride) for 30 min of 28 g/g or more.

10. The preparation method of a super absorbent polymer of claim 1,
    wherein the super absorbent polymer has an absorbency under pressure (AUP) at 0.7 psi of 23 to 27 g/g, measured according to EDANA method WSP 242.3-10.

11. The preparation method of a super absorbent polymer of claim 1,
    wherein the super absorbent polymer has a saline (0.685 wt % aqueous solution of sodium chloride) flow conductivity (SFC; $\cdot 10^{-7}$ cm$^3$·s/g) of 30 ($\cdot 10^{-7}$ cm$^3$·s/g) or more.

12. The preparation method of a super absorbent polymer of claim 1,
    wherein the super absorbent polymer has a vortex time of 5 to 50 seconds by a vortex method, and
    wherein the vortex method comprises:
    adding an amount of the super absorbent polymer to a saline solution at a temperature of 23° C. to 24° C.,
    stirring the super absorbent polymer in the saline solution using a magnetic bar at 600 rpm to produce a vortex, and
    measuring a time until the vortex disappears.

13. The preparation method of a super absorbent polymer of claim 1, wherein the super absorbent polymer has a centrifuge retention capacity (CRC) of saline (0.9 wt % aqueous solution of sodium chloride) for 30 min of 40 g/g or less.

14. The preparation method of a super absorbent polymer of claim 1, wherein the super absorbent polymer has a saline (0.685 wt % aqueous solution of sodium chloride) flow conductivity (SFC; $\cdot 10^{-7}$ cm$^3$·s/g) of 70 ($\cdot 10^{-7}$ cm$^3$·s/g) or less.

15. The preparation method of a super absorbent polymer of claim 1, wherein the dynamic pressure applied to the monomer mixture is adjusted to be within the range of 0.150 to 1,000 kPa.

* * * * *